US007699059B2

(12) United States Patent
Fonseca et al.

(10) Patent No.: US 7,699,059 B2
(45) Date of Patent: Apr. 20, 2010

(54) IMPLANTABLE WIRELESS SENSOR

(75) Inventors: Michael Fonseca, Atlanta, GA (US); Mark Allen, Atlanta, GA (US); David Stern, Grayson, GA (US); Jason White, Atlanta, GA (US); Jason Kroh, Villa Rica, GA (US)

(73) Assignee: CardioMEMS, Inc., Atlanta, GA (US)

( * ) Notice: Subject to any disclaimer, the term of this patent is extended or adjusted under 35 U.S.C. 154(b) by 494 days.

(21) Appl. No.: 10/054,671

(22) Filed: Jan. 22, 2002

(65) Prior Publication Data
US 2003/0136417 A1 Jul. 24, 2003

(51) Int. Cl.
*A61F 13/00* (2006.01)
*A61B 5/02* (2006.01)

(52) U.S. Cl. ..................... 128/899; 600/486

(58) Field of Classification Search ............... 128/899, 128/903; 600/481–486, 488, 552, 553, 561, 600/587
See application file for complete search history.

(56) References Cited

U.S. PATENT DOCUMENTS

| 2,796,863 | A | 6/1957 | von Wittern |
| 3,867,950 | A | 2/1975 | Fischell |
| 3,942,382 | A | 3/1976 | Hok |
| 3,958,558 | A | 5/1976 | Dunphy et al. |
| 4,026,276 | A | 5/1977 | Chubbuck |
| 4,127,110 | A | 11/1978 | Bullara |
| 4,206,762 | A | 6/1980 | Cosman |
| 4,207,903 | A | 6/1980 | O'Neill |
| RE30,366 | E | 8/1980 | Rasor et al. |
| 4,237,900 | A | 12/1980 | Schulman et al. |
| 4,354,506 | A | 10/1982 | Sakaguchi et al. |
| 4,378,809 | A | 4/1983 | Cosman |
| 4,485,813 | A | 12/1984 | Anderson et al. |
| 4,494,950 | A | 1/1985 | Fischell |
| 4,521,684 | A | 6/1985 | Gilby et al. |
| 4,593,703 | A | 6/1986 | Cosman |
| 4,596,563 | A | 6/1986 | Pande |

(Continued)

FOREIGN PATENT DOCUMENTS

CA    1 158 061    6/1983

(Continued)

OTHER PUBLICATIONS

M. Gawenda, J. Heckenkamp, M. Zaehringer, J. Brunkwall; "Intra-Aneurysm Sac Pressure—The Holy Gail of Endoluminal Grafting of AAA"; Eur J Vasc Endovasc Surg, vol. 24, Aug. 2002, pp. 139-145.

(Continued)

*Primary Examiner*—John P Lacyk
(74) *Attorney, Agent, or Firm*—Kilpatrick Stockton LLP

(57) ABSTRACT

The progress of a endovascular aneurysm repair can be monitored by inserting a pressure transducer sensor using a catheter into the sac during endovascular aneurysm repair and then using a small, hand-held read out device to measure pressure easily, safely, inexpensively and accurately. In one aspect a sensor is introduced into the body by the steps of folding or rolling the sensor into a cylinder, loading it into a catheter, and deploying into the aneurysm sac by allowing it to unroll or unfold, either by itself or facilitated by the incorporation of a super-elastic alloy component.

44 Claims, 15 Drawing Sheets

U.S. PATENT DOCUMENTS

| | | | |
|---|---|---|---|
| 4,713,540 A | 12/1987 | Gibly et al. |
| 4,718,425 A | 1/1988 | Tanaka et al. |
| 4,796,641 A | 1/1989 | Mills et al. |
| 4,815,472 A | 3/1989 | Wise et al. |
| 4,846,191 A | 7/1989 | Brockway et al. |
| 4,890,623 A | 1/1990 | Cook et al. |
| 4,899,752 A | 2/1990 | Cohen |
| 4,913,147 A | 4/1990 | Fahlstrom et al. |
| 4,934,369 A | 6/1990 | Maxwell |
| 4,987,897 A | 1/1991 | Funke |
| 5,113,868 A | 5/1992 | Wise et al. |
| 5,115,128 A | 5/1992 | Cook |
| 5,129,394 A | 7/1992 | Mehra |
| 5,131,399 A | 7/1992 | Sciarra |
| 5,165,289 A | 11/1992 | Tilmans |
| 5,181,423 A | 1/1993 | Philipps et al. |
| 5,192,314 A | 3/1993 | Daskalakis |
| 5,207,103 A | 5/1993 | Wise et al. |
| 5,265,606 A | 11/1993 | Kujawski |
| 5,353,800 A | 10/1994 | Pohndorf et al. |
| 5,367,376 A | 11/1994 | Lagakas et al. |
| 5,373,852 A | 12/1994 | Harrison et al. |
| 5,411,551 A | 5/1995 | Winston et al. |
| 5,431,171 A | 7/1995 | Harrison et al. |
| 5,440,300 A | 8/1995 | Spillman, Jr. |
| 5,487,760 A | 1/1996 | Villafana |
| 5,497,099 A | 3/1996 | Walton |
| 5,515,041 A | 5/1996 | Spillman, Jr. |
| 5,535,752 A | 7/1996 | Halperin et al. |
| 5,538,005 A | 7/1996 | Harrison et al. |
| 5,551,427 A | 9/1996 | Altman |
| 5,566,676 A | 10/1996 | Rosenfeldt et al. |
| 5,583,474 A | 12/1996 | Mizoguchi et al. |
| 5,593,430 A | 1/1997 | Renger |
| 5,600,245 A | 2/1997 | Yamamoto et al. |
| 5,626,630 A | 5/1997 | Markowitz et al. |
| 5,686,841 A | 11/1997 | Stolarczyk et al. |
| 5,695,155 A | 12/1997 | Macdonald et al. |
| 5,702,427 A | 12/1997 | Ecker et al. |
| 5,703,576 A | 12/1997 | Spillman, Jr. et al. |
| 5,713,917 A | 2/1998 | Leonhardt et al. |
| 5,722,414 A | 3/1998 | Archibald et al. |
| 5,723,791 A | 3/1998 | Koch et al. |
| 5,743,267 A | 4/1998 | Nikolic et al. |
| 5,796,827 A | 8/1998 | Coppersmith et al. |
| 5,807,265 A | 9/1998 | Itoigawa et al. |
| 5,836,886 A | 11/1998 | Itoigawa et al. |
| 5,860,938 A | 1/1999 | Lafontaine et al. |
| 5,899,927 A | 5/1999 | Ecker et al. |
| 5,935,084 A | 8/1999 | Southworth |
| 5,942,991 A | 8/1999 | Gaudreau et al. |
| 5,967,986 A | 10/1999 | Cimochowski et al. |
| 6,015,386 A | 1/2000 | Kensey et al. |
| 6,015,387 A | 1/2000 | Schwartz et al. |
| 6,019,729 A | 2/2000 | Itoigawa et al. |
| 6,024,704 A | 2/2000 | Meador et al. |
| 6,025,725 A | 2/2000 | Gershenfeld et al. |
| 6,030,413 A | 2/2000 | Lazarus |
| 6,033,366 A | 3/2000 | Brockway et al. |
| 6,053,873 A | 4/2000 | Govari et al. |
| 6,076,016 A | 6/2000 | Feierbach |
| 6,111,520 A * | 8/2000 | Allen et al. ............ 340/870.16 |
| 6,113,553 A | 9/2000 | Chubbuck |
| 6,134,461 A | 10/2000 | Say et al. |
| 6,140,740 A | 10/2000 | Porat et al. |
| 6,159,156 A | 12/2000 | Van Bockel |
| 6,198,965 B1 | 3/2001 | Penner et al. |
| 6,201,980 B1 * | 3/2001 | Darrow et al. ............ 600/347 |
| 6,206,835 B1 | 3/2001 | Spillman et al. |
| 6,229,190 B1 | 5/2001 | Bryzek et al. |
| 6,237,398 B1 | 5/2001 | Porat et al. |
| 6,239,724 B1 | 5/2001 | Doron et al. |
| 6,277,078 B1 | 8/2001 | Porat et al. |
| 6,278,379 B1 | 8/2001 | Allen et al. |
| 6,287,253 B1 | 9/2001 | Ortega et al. |
| 6,373,264 B1 | 4/2002 | Matsumoto et al. |
| 6,400,974 B1 | 6/2002 | Lesho |
| 6,409,674 B1 | 6/2002 | Brockway et al. |
| 6,442,413 B1 | 8/2002 | Silver |
| 6,454,720 B1 | 9/2002 | Clerc et al. |
| 6,645,143 B2 | 11/2003 | Van Tassell et al. |
| 6,667,725 B1 | 12/2003 | Simons et al. |
| 6,682,490 B2 | 1/2004 | Roy et al. |
| 6,765,493 B2 | 7/2004 | Lonsdale et al. |
| 6,855,115 B2 | 2/2005 | Fonseca et al. |
| 6,923,769 B2 | 8/2005 | Nishii et al. |
| 6,926,670 B2 | 8/2005 | Rich et al. |
| 6,939,299 B1 | 9/2005 | Petersen et al. |
| 2002/0077556 A1 | 6/2002 | Schwartz et al. |
| 2002/0151816 A1 | 10/2002 | Rich et al. |
| 2002/0188207 A1 | 12/2002 | Richter |
| 2003/0031587 A1 | 2/2003 | Hu et al. |
| 2003/0136417 A1 | 7/2003 | Fonseca et al. |
| 2003/0139677 A1 | 7/2003 | Fonseca et al. |
| 2004/0122494 A1 | 6/2004 | Eggers et al. |
| 2005/0075697 A1 | 4/2005 | Olson et al. |
| 2005/0085703 A1 | 4/2005 | Behm |
| 2005/0154321 A1 | 7/2005 | Wolinsky et al. |

FOREIGN PATENT DOCUMENTS

| | | |
|---|---|---|
| DE | 196 44 858.5 | 10/1996 |
| EP | 0257801 | 3/1988 |
| EP | 0 337 035 | 11/1993 |
| EP | 0 646 365 | 4/1995 |
| WO | WO 83/03348 | 10/1983 |
| WO | WO 90/06723 | 6/1990 |
| WO | WO 95/33517 | 12/1995 |
| WO | WO 97/09926 | 3/1997 |
| WO | WO 97/32518 | 9/1997 |
| WO | WO 97/32519 | 9/1997 |
| WO | WO 97/33513 | 9/1997 |
| WO | WO 99/34731 | 7/1999 |
| WO | WO 99/42176 | 8/1999 |
| WO | WO 99/62587 | 12/1999 |
| WO | WO 00/16686 | 3/2000 |
| WO | WO 01/00089 | 1/2001 |
| WO | WO 01/87137 | 11/2001 |
| WO | WO 01/97908 | 12/2001 |
| WO | WO 02/058551 | 8/2002 |
| WO | WO 03/061467 | 7/2003 |
| WO | WO 03/061504 | 7/2003 |
| WO | WO 03/096889 | 11/2003 |

OTHER PUBLICATIONS

G.W.H. Schurink, N.J.M. Arts, J.M Van Baalen, L.J. Schultze Kool, J.H. Van Bockel; "Experimental Study Of The Influence Of Endoleak Size On Pressure In The Aneurysm Sac And The Consequences Of Thrombosis"; Bristish Journal of Surgery 2002, 87 pp. 71-78.

B. Sonesson, N. Dias, M. Malina, P. Olofsson, D. Griffin, B. Lindblad, K. Ivancev; "Intra-Aneurysm Pressure Measurements in Successfully Excluded Abdominal Aortic Aneurysm After Endovascular Repair"; Journal of Vascular Surgery, vol. 37, No. 4, Apr. 2003; pp. 733-738.

C.S. Skillern, S.L. Stevens, K.T. Piercy, R.L. Donnell, M. B. Freeman, M.H. Goldman; "Endotension In An Experiemental Aneurysm Model"; Journal of Vascular Surgery, vol. 36, No. 4, Oct. 2002, pp. 814-817.

G.D. Treharne, I.M. Loftus, M.M. Thompson, N. Lennard, J. Smith, G. Fishwick, P.R.F. Bell; "Quality Control During Endovascular Aneurysm Repair: Monitoring Aneurysmal Sac Pressure and Superficial Femoral Artery Flow Velocity"; J. Endovasc Surg, 1999, 6, p. 239-245.

M.L. Manwaring, V.D. Malbasa, K.L. Manwaring: "Remote Monitoring of Intracranial Pressure"; Institute of Concology; Annals of The Academy of Studenica Apr. 2001; pp. 77-80.

R.A. Baum, J.P. Carpenter, C. Cope, M.A. Golden, O.C. Velazquez, D.G. Neschis, M.E. Mitchell, C.F. Barker, R.M. Fairman; "Aneurysm Sac Pressure Measurements After Endovascular Repair of Abdominal Aortic Aneurysms"; Journal of Vascular Surgery, vol. 33, No. 1, Jan. 2001, pp. 32-41.

P.L. Harris, S. Dimitri; "Predicting Failure Of Endovascular Aneurysm Repair"; Eur J Vas Endovasc Surg, vol. 17, Jan. 1999; pp. 1-2.

K.F. Adams, Jr.; "Guiding Heart Failure Care by Invasive Hemodynamic Measurements: Possible or Useful?"; Journal of Cardiac Failure, vol. 8, No. 2, Apr. 2002, pp. 71-73.

Failure; Journal of Cardiac Failure, vol. 8, No. 2, Apr. 2002, pp. 63-70.

R. Shabetai; "Monitoring Heart Failure Hemodynamics With An Implanted Device: Its Potential To Improve Outcome"; Journal of the American College of Cardiology; vol. 41, No. 4, Feb. 19, 2003; pp. 572-573.

J.C. Parodi, R. Berguer, L.M. Ferreira, R. Lamura, M.L. Schermerhorn; "Intra-eneurysmal Pressure After Incomplete Endovascular Exclusion"; Journal of Vascular Surgery, vol. 34, No. 5, Nov. 2001, pp. 909-914.

T. Chuter, K. Ivancev, M. Malina, T. Resch, J. Brunkwall, B. Lindblad, B. Risberg; "Endovascular And Surgical Techniques"; Eur J. Vasc Endovasc Surg vol. 13, Jan. 1997, pp. 85-87.

J.T. Farrar, C. Berkley, V.K. Zworykin; "Telemetering Of Intraenteric Pressure In Man By An Externally Energized Wireless Capsule"; Science, New Series, vol. 131, Issue 3416 (Jun. 17, 1960), 1814.

Sanchez, et al., Chronic Intraaneurysmal pressure measurements: an experimental method for evaluating the effectiveness of endovascular aortic aneurism exclusion; J. Vasc. Surg. Vo. 26, No. 2, Aug. 1997.

Collins, et al., Miniatrure Passive Pressure Transensor for Implanting in the Eye; IEEE Transactions on Bio-Medical Engineering vol. BME-14, No. 2, pp. 74-83, Apr. 1967.

Criado, et al., An Aortic Aneurysm model for the evaluation of endovascular exclusion prostheses; J. Vasc. Surg. vol. 22, No. 3, Sep. 1995.

* cited by examiner

IMPLANTABLE WIRELESS SENSOR

FIELD OF THE INVENTION

The application is directed to an implantable wireless sensor. More particularly, this invention is directed to a wireless, unpowered, micromechanical, flexible sensor that can be delivered using endovascular techniques, to measure a corporeal parameter such as pressure or temperature.

BACKGROUND OF THE INVENTION

Abdominal aortic aneurysms represent a dilatation and weakening of the abdominal aorta which can lead to aortic rupture and sudden death. Previously, the medical treatment of abdominal aortic aneurysms required complicated surgery with an associated high risk of injury to the patient. More recently, endografts (combining stents and grafts into a single device) have been developed that can be inserted through small incisions in the groin. Once in place, these endografts seal off the weakened section of the aorta. The aneurysms can then heal, eliminating the risk of sudden rupture. This less invasive form of treatment for abdominal aortic aneurysms has rapidly become the standard of care for this disease. An example of an endograft device is disclosed in Kornberg, U.S. Pat. No. 4,617,932.

A significant problem with endografts is that, due to inadequate sealing of the graft with the aorta, leaks can develop that allow blood to continue to fill the aneurysmal sac. Left undiscovered, the sac will continue to expand and potentially rupture. To address this situation, patients who have received endograft treatment for their abdominal aortic aneurysms are subjected to complex procedures that rely on injection of contrast agents to visualize the interior of the aneurysm sac. These procedures are expensive, not sensitive, and painful. In addition, they subject the patient to additional risk of injury. See for example, Baum R A et al., "Aneurysm sac pressure measurements after endovascular repair of abdominal aortic aneurysms", *The Journal of Vascular Surgery*, January 2001, and Schurink G W et al., "Endoleakage after stent-graft treatment of abdominal aneurysm: implications on pressure and imaging—an in vitro study", *The Journal of Vascular Surgery*, August 1998. These articles provide further confirmation of the problem of endograft leakage and the value of intra-sac pressure measurements for monitoring of this condition.

Thus, there is a need for a method of monitor the pressure within an aneurysm sac that has undergone repair by implantation of an endograft to be able to identify the potential presence of endoleaks. Furthermore, this method should be accurate, reliable, safe, simple to use, inexpensive to manufacture, convenient to implant and comfortable to the patient.

An ideal method of accomplishing all of the above objectives would be to place a device capable of measuring pressure within the aneurysm sac at the time of endograft insertion. By utilizing an external device to display the pressure being measured by the sensor, the physician will obtain an immediate assessment of the success of the endograft at time of the procedure, and outpatient follow-up visits will allow simple monitoring of the success of the endograft implantation.

An example of an implantable pressure sensor designed to monitor pressure increases within an aneurysmal sac is shown in Van Bockel, U.S. Pat. No. 6,159,156. While some of the above objectives are accomplished, this device has multiple problems that would make its use impractical. For example, the sensor disclosed in the Van Bockel patent relies on a mechanical sensing element. Elements of this kind cannot be practically manufactured in dimensions that would allow for endovascular introduction. In addition, this type of pressure sensor would be subject to many problems in use that would limit its accuracy and reliability. One example would be exposure of the mechanical sensing element to body fluids which could disrupt its function. Also, by failing to take advantage of specific approaches to electronic component fabrication, the Van Bockel device requires a complex system for acquiring data from the sensor necessary for the physician to make an accurate determination of intra-aneurysmal pressure. The Van Bockel device would inherently not be as flexible as required for certain endovascular or percutaneous procedures.

OBJECTS OF THE INVENTION

It is an object of this invention to provide an implantable wireless sensor.

It is also an object of this invention to provide a wireless, unpowered micromechanical, flexible sensor that can be delivered endovascularly.

It is a further object of this invention to provide an implantable, wireless, unpowered sensor that can be delivered endovascularly to measure pressure and/or temperature.

It is a yet further object of this invention to provide a method of preparing a micromechanical implantable sensor.

These and other objects of the invention will become more apparent from the discussion below.

SUMMARY OF THE INVENTION

The present invention comprises a device that can be implanted into the human body using non-surgical techniques to measure a corporeal parameter such as pressure, temperature, or both. Specific target locations could include the interior of an abdominal aneurysm or a chamber of the heart. This sensor is fabricated using MicroElectroMechanical Systems (MEMS) technology, which allows the creation of a flexible device that is small, accurate, precise, durable, robust, biocompatible, radiopaque and insensitive to changes in body chemistry, biology or external pressure. This device will not require the use of wires to relay pressure information externally nor need an internal power supply to perform its function.

The MEMS approach to sensor design lends itself to the fabrication of small, flat flexible sensors that can be formed using biocompatible polymers as substrate materials. The pressure sensor described above can then be manipulated into a smaller shape and size by rolling, bending, or folding it into a cylindrical form. This smaller object can be introduced into the sac of an abdominal aneurysm at the time an endograft is deployed within the aorta by using standard endovascular catheter techniques. Once inserted in the abdominal aneurysm sac or in a chamber of the heart, the device either on its own or through the addition or inclusion of metallic elements fabricated from stainless steel or super-elastic or shape memory nitinol alloys can unfurl into a preferred flat shape. The metallic components may also include anchors, hooks, harpoons, coils, barbs or other shapes and configurations designed to secure the pressure sensor to the wall on the aneurysm sac or a chamber of the heart. In addition, appropriately biocompatible coatings may be applied to the surface of the sensor to prevent adhesion of biological substances or coagulated blood to the sensor that could interfere with its proper function.

Delivery of the device of the invention to an aneurysm may be accomplished as follows: Using the standard Seldinger technique, the physician gains access to the patient's femoral artery and places a vessel introducer with a hemostatic valve. Under direct fluoroscopic visualization, a flexible guidewire is inserted through the introducer catheter and maneuvered such that its tip is stationed within the sac of the aortic aneurysm. A coaxial delivery catheter consisting of two hollow extruded polymeric catheters, the smaller of the two disposed inside the larger one, is inserted over the guidewire and through the introducer and advanced distally until its tip is within the aneurysmal sac. The smaller catheter has an annular space to hold a folded sensor, which is released when the outer catheter is withdrawn proximally.

In an alternative delivery procedure, a sensor is attached to a small diameter, proximally extending "safety" or tether wire. The sensor and safety wire are also positioned in the annular space between two coaxial catheters, but the safety wire runs the entire length of the smaller delivery catheter and extends proximally past the proximal end of that catheter outside the patient. In this configuration, the sensor remains secured to the tether wire after the coaxial delivery catheter is removed from the patient. Following the insertion and deployment of the stent-graft, the sensor is detached from the tether wire using any of the methods known in the art, and the wire is removed.

In a further alternative delivery procedure the sensor can be loaded into the annular space between the inner and outer catheters by inserting the sensor into a longitudinal slit cut into the outer catheter and attaching a tab on the sensor's surface into a slot cut into the inner coaxial catheter. By rotation of the inner tube, the sensor will be retracted through the slit and positioned in the annular space between the two tubes. To deploy the device, the rotation of the inner tube is reversed and the sensor emerges through the slit of the outer catheter. There are two specific advantages to this deployment mechanism. First, the sensor can be packaged and stored in a flat configuration. This is desirable since long term storage in a pre-loaded curved geometry could make it more difficult for the sensor to re-establish the flat arrangement that is optimal for effective electromagnetic inductive coupling with the external read-out unit. The second advantage is that by cutting the longitudinal slit at angle that is offset from the main axis of the outer tube, the sensor will be biased into a planar configuration as it is forced through the slit during the deployment process.

A safety wire system can also be used with this mechanism, although the wire may be external to the outer coaxial tube. As described above, the wire will remain attached to the sensor during the deployment process and will stay within the aneurysm sac while the delivery catheter is removed. Subsequent to insertion and deployment of the stent-graft, the wire will be detached from the sensor and pulled out of the body.

The detachment of the wire from the sensor can be accomplished in several ways. The wire may be simply glued to the sensor using an adhesive. To separate the sensor from the wire, a thin-walled, metal or polymer tube is passed along the length of the wire and positioned at the adhesive joint. While holding this tube steady, the wire is then retracted into the tube. Sufficient traction can be applied to the segment of the wire that remains outside of the body to cause the adhesive to joint to fail and allow removal of the wire.

An alternative method would rely on a mechanical connection between the wire and sensor such as adding threads to the end of the wire which could then be connected to a matching threaded female receptacle on the sensor. To separate the wire from the sensor, counter-rotation would be applied to the wire until the threads disengage. One could envision many variations of this design that would involve the mechanical locking and un-locking of two mating components.

In a delivery system intended more for cardiac applications, a "daisy shape" sensor is positioned in the distal end of a catheter lumen so that the middle, flat section of the sensor is essentially normal to the longitudinal axis of the catheter. A solid or hollow member fitting within the catheter lumen is used to push the sensor distally. If the sensor has an anchor member, it is meant that the anchor member will pierce or otherwise attach itself and the sensor to the wall of a chamber of the heart.

DETAILED DESCRIPTION OF THE INVENTION

Figure 1:
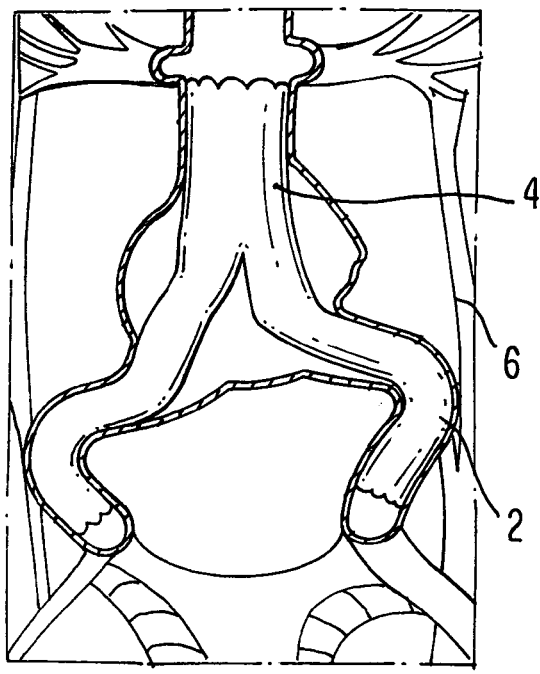
FIG. 1 is a partly cross-sectional view of an aortic abdominal aneurysm stent after placement in a patient.

The invention can perhaps be better understood by referring to the drawings. FIG. 1 represents a typical abdominal aortic aneurysm stent 2 that has been inserted into an abdominal aorta 4. Stent 2, which typically comprises a polymeric material, creates passageways within an aneurysm sac 6.

Figure 2:
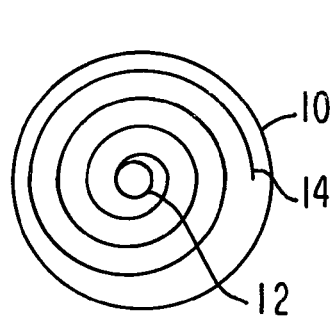
FIG. 2 is a front view of an embodiment of the invention.
Figure 3:
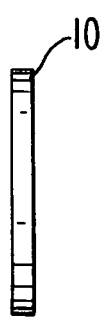
FIG. 3 is a lateral view of the embodiment of the invention shown in FIG. 2.
Figure 4:
FIG. 4 is a lateral view of an embodiment of the invention of FIG. 2 folded for delivery.

One embodiment of a sensor according to the invention is shown in FIGS. 2, 3, and 4, where a disc-shaped sensor 10 comprises a capacitor disk 12 and a wire spiral 14. FIG. 3 is a lateral view of sensor 10, and FIG. 4 is a lateral view of sensor 10 in a folded configuration for insertion. The fact that sensor 10 is sufficiently flexible to be folded as shown in FIG. 4 is an important aspect of the invention.

Figure 5:
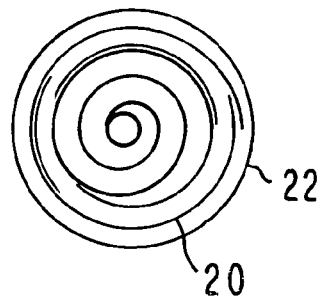
FIG. 5 is a front view of another embodiment of the invention.
Figure 6:
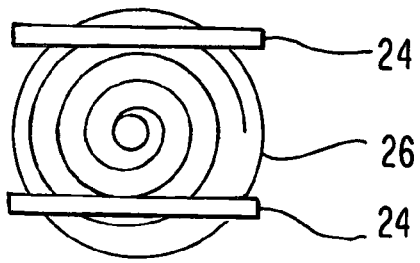
FIG. 6 is a front view of further embodiment of the invention.

In FIG. 5 a ring 20 comprised of a shape memory alloy such as nitinol has been attached to, for example, with adhesive, or incorporated into, for example, layered within, a sensor 22, and in FIG. 6 strips 24 comprised of a shape memory alloy such as nitinol have been attached to a sensor 26.

Figure 7:
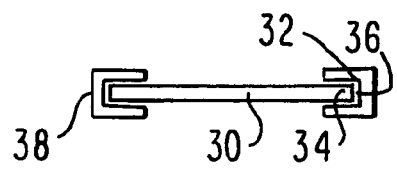
FIG. 7 is a lateral view of a yet further embodiment of the invention.

FIG. 7 is a lateral cross-sectional view of a circular sensor 30 having a ring 32 comprised of a shape memory alloy such as nitinol encompassing the outer edge 34 of sensor 30. Ring 32 preferably is attached to outer edge 34 by a suitable physiologically acceptable adhesive 36, such as an appropriate epoxy or cyanoacrylate material. Preferably the ring will be radiopaque.

The size of the circular sensors of the invention will vary according to factors such as the intended application, the delivery system, etc. The circular sensors are intended to be from about 0.5 to about 3 cm in diameter, with a thickness of from about 0.05 to about 0.30 in. When a ring 32 is employed, the thickness of the ring, i.e., the width of the outside surface 38, will preferably be from about 1.5 to about 3.5 times the thickness of the sensor.

Figure 8A:
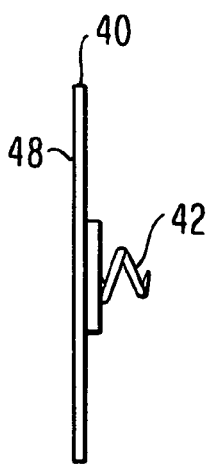
FIGS. 8A and 8B are each a lateral view of an embodiment of the invention with an anchoring mechanism.
Figure 8B:
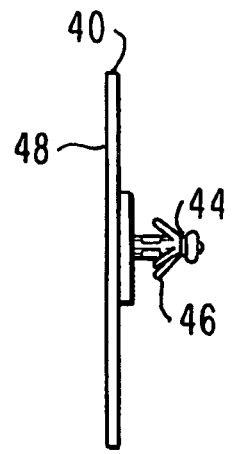

FIGS. 8A and 8B each represent a lateral view of a sensor with an anchoring member. In FIG. 8A sensor 40 has a screw/coil 42, and in FIG. 8B sensor 40 has an anchor 44 with umbrella-like projections 46. When pressure is applied to the flat side 48 of sensor 40, anchor 42 or 44 will penetrate a vessel wall, organ wall, or other substrate to cause sensor 36 to remain in a desired position or location. Alternatively, an anchoring mechanism such as is shown in FIGS. 8A and 8B could be attached to ring 32 in FIG. 7.

Figure 9:
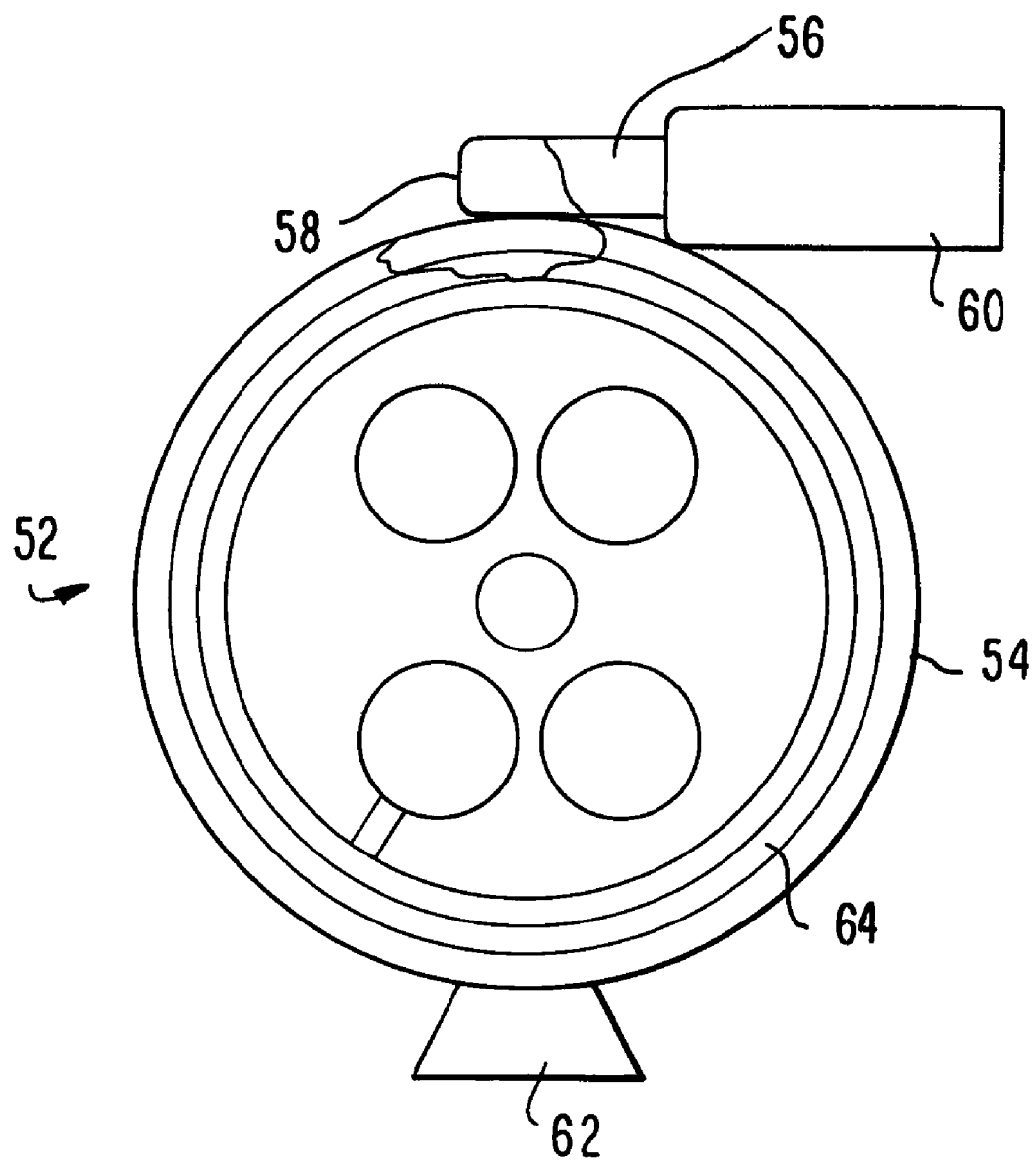
FIG. 9 is a schematic of an alternate shape for a sensor of the invention.

In the embodiment of the invention shown in FIG. 9, a sensor 52 has an outer flat surface 54. A safety or tether wire 56 is attached to sensor 52 at an adhesive point 58, and tether wire 58 is positioned slidably within a tether detachment sheath 60. Adhesive point 58 will preferably comprise a physiologically acceptable settable adhesive material such as an epoxy or a cyanoacrylate. When sheath 62 is moved distally, tether wire 56 is severed from sensor 52. A loading tab 62 is useful for positioning sensor 52 in a delivery catheter (not shown here); however, loading tab 62 is designed or intended to be broken off, or sacrificed, during delivery. An optimal shape memory alloy ring element, such as a nitinol disk 64 attached to surface 54 or layered therein, assists the sensor in attaining a flat shape upon release.

Figure 10:
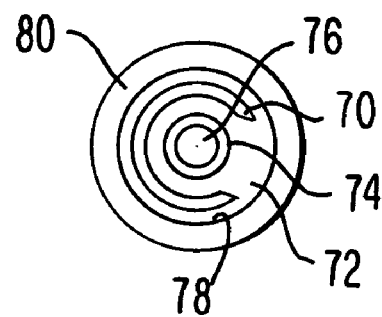
FIG. 10 is a cross-sectional view of a delivery catheter according to the invention.
Figure 11:
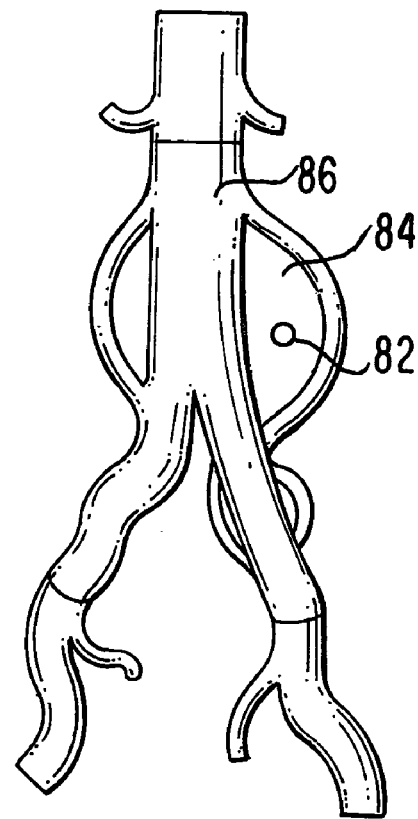
FIG. 11 is a schematic depicting placement of an embodiment of the invention in an aneurysm.

Prior to insertion of the coaxial catheter, as shown in FIG. 10, a sensor 70 is rolled into the shape of a small diameter cylinder and placed into the annular space 72 defined by the outside wall 74 of a smaller diameter catheter 76 and the inner wall 78 of a larger diameter catheter 80. Once in position within an aneurysm sac, force is applied in the proximal direction to outer coaxial catheter 80. This action exposes cylindrically shaped sensor 70, which, free of the constraint of outer catheter 80, springs into its initial flat shape and is deposited within an aneurysm sac prior to the introduction of a stent-graft. If the sensor has any of the anchors, hooks, harpoons, coils, barbs or other shapes and configurations of metallic elements described above, the catheter may be pressed to secure the pressure sensor to the aneurysm sac wall, as shown in FIG. 11, wherein a sensor 82 is positioned within aneurysm sac 84 adjacent aortic stent 86.

Figure 12:
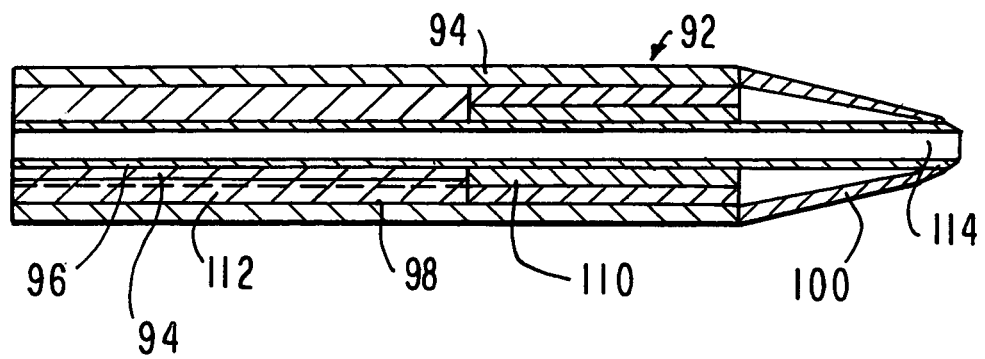
FIG. 12 is a schematic representation of an embodiment of the invention with distributed capacitance.

A better appreciation of certain aspects of the invention, especially of a delivery system, can be obtained from FIG. 12, where a catheter 92 comprises an outer tubular member 94 and an inner coaxial shaft member 96. The distal end of shaft member 96 comprises an atraumatic tip 100. A sensor 110 is positioned around shaft member 96 in an annular space 102 proximal to atraumatic tip 100. When outer tubular member 94 is withdrawn in the proximal direction, sensor 110 is released and uncoils. Preferably a tether wire 98 attached to sensor 110 extends proximally in a groove 112 in shaft member 96. Coaxial shaft member 96 preferably has a lumen 114 so that the delivery system can be advanced over a guidewire (not shown).

Figure 13:
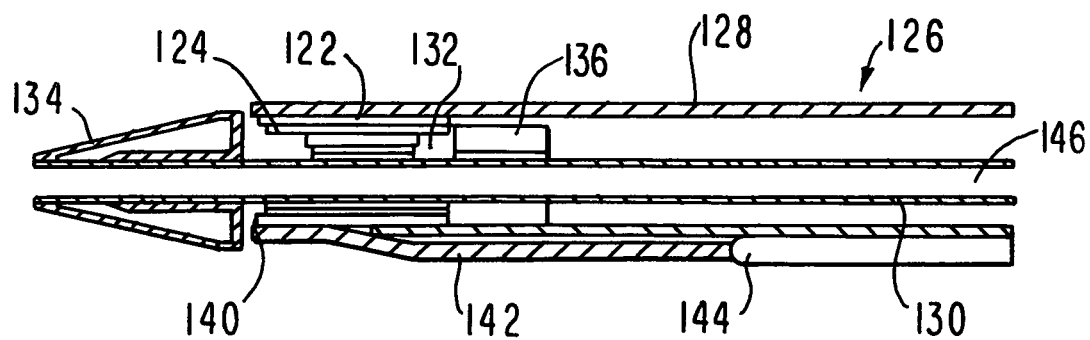
FIG. 13 is a cross-sectional view of the distal end of a delivery catheter with the embodiment shown in FIG. 9

In another embodiment of the invention, seen in FIG. 13, a sensor 122, preferably with a nitinol ring 124 that biases the sensor into a flat configuration after deployment, is positioned within a delivery catheter 126 comprising outer tubular member 128 and inner catheter shaft member 130. Sensor 122 is coiled in an annular space 132 formed between an atraumatic tip 134 and a stop member 136. An adhesive attachment point 140 attaches sensor 122 to a tether wire 142, which extends into a proximally extending tether detachment sheath 144. Preferably inner shaft member 130 has a lumen 146 so that the delivery catheter 126 depicted can be advanced over a guidewire (not shown).

Figure 14:
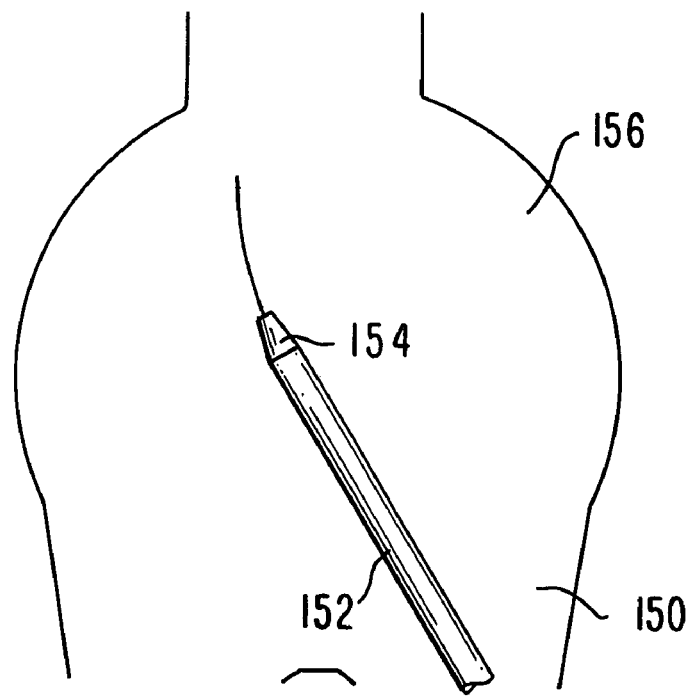
FIGS. 14 to 19 are schematic representations of different steps of the delivery of a sensor according to the invention.
Figure 15:
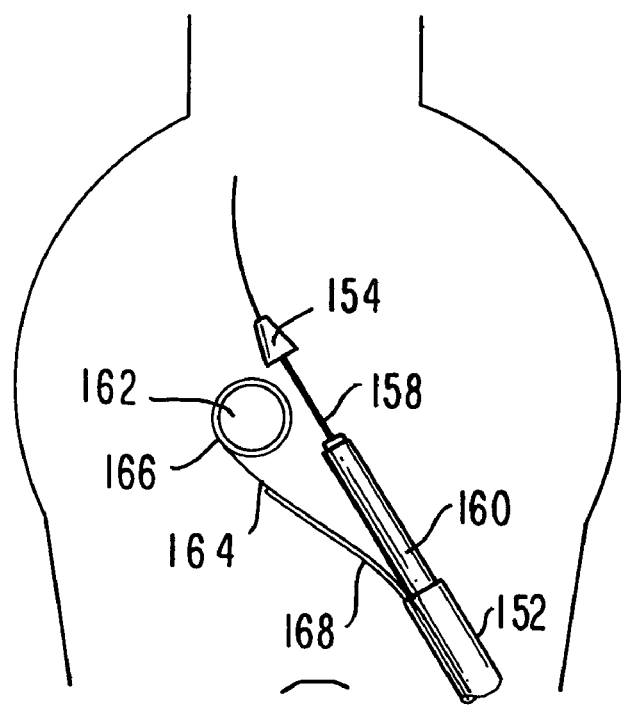

Actual delivery of a sensor according to the invention is shown in FIGS. 14 to 20. A loaded delivery system 150 has an outer tubular member 152 coaxial to an inner catheter (not shown) that terminates in a distal atraumatic tip 154, and atraumatic tip 154 is advanced into an abdominal aortic aneurysm area 156, as shown in FIG. 14. Then, outer tubular member 152 is retracted to expose an annular area 158 in inner catheter 160 and release a sensor 162 attached to a tether wire 164 through adhesive area 166, as shown in FIG. 15. Tether wire 164 extends into tether sheath 168.

Figure 16:
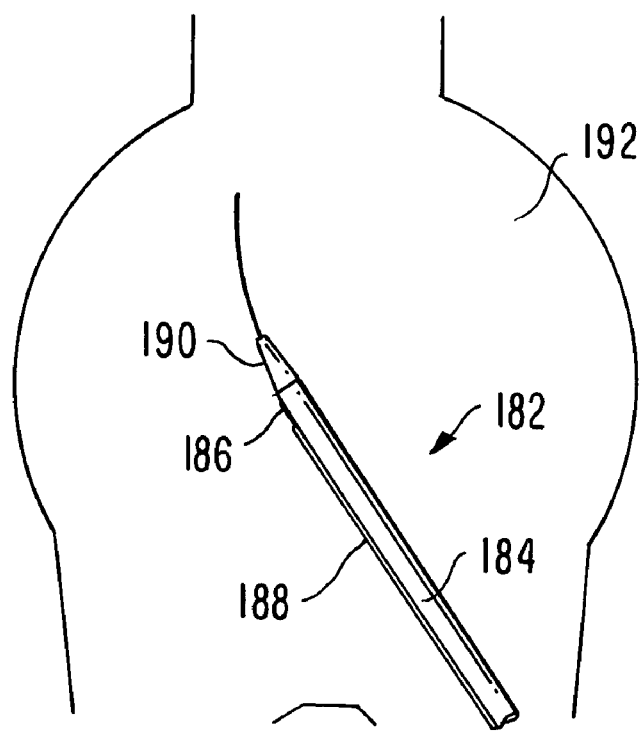
Figure 17:
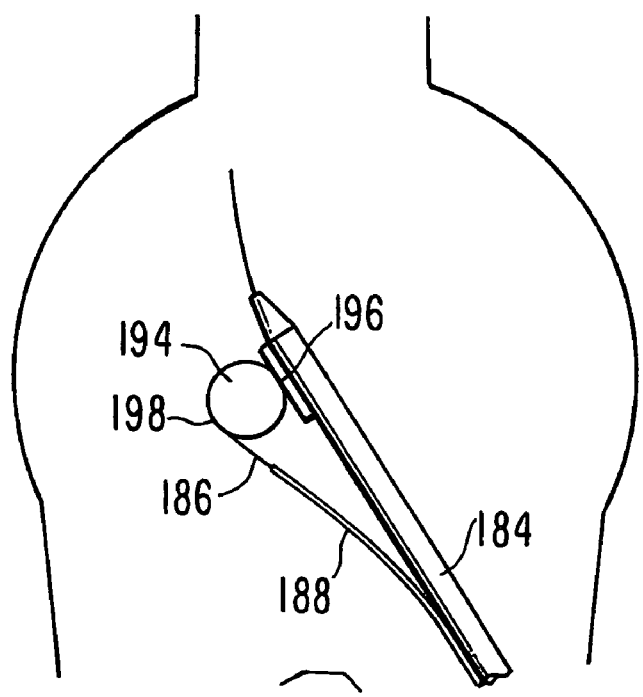

In FIG. 16, a coaxial delivery system 182 comprising an outer tubular member 184 and an inner catheter (not shown) and having a tether wire 186 with a tether sheath 188 and an atraumatic tip 190 is advanced into an abdominal aortic aneurysm area 192. The coaxial catheters are rotated to cause a sensor 194 to pass through a slit 196 in outer coaxial catheter 184, as shown in FIG. 17. Sensor 194 is attached to tether wire 186 at adhesive point 198. Sensor 194 is then tested, with the option that if sensor 194 is inoperative, it can be rolled back into slit 196.

Figure 18:
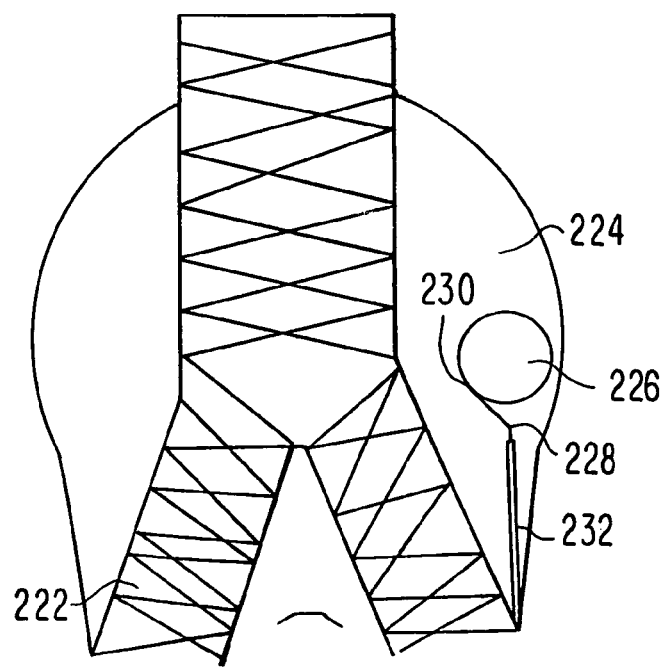
Figure 19:
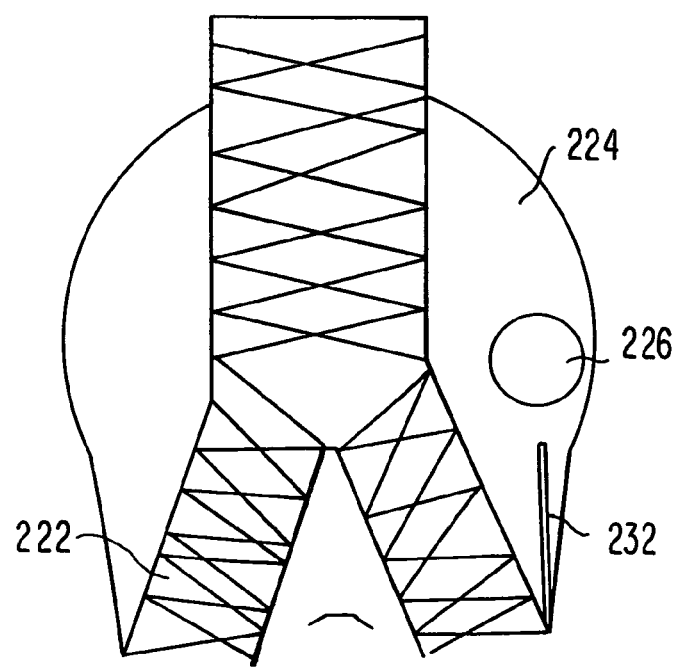

When either delivery system 150 or 182 is retracted, sensor 162 or 194 is left positioned to the side of an aneurysm. Then, as shown in FIG. 18, a stent graft 222 is deployed in an aneurysm sac 224. Where a sensor 226 was attached to tether wire 228 at adhesive point 230, a tether sheath 232 is moved distally to free sensor 226 from tether wire 228. See, FIG. 19.

The pressure sensor of the invention can be manufactured using Micro-machining techniques that were developed for the integrated circuit industry. An example of this type of sensor features an inductive-capacitive (LC) resonant circuit with a variable capacitor, as is described in Allen et al., U.S. Pat. No. 6,111,520, all of which is incorporated herein by reference. The sensor contains two types of passive electrical components, namely, an inductor and a capacitor. The sensor is constructed so that the fluid pressure at the sensor's surface changes the distance between the capacitor's parallel plates and causes a variation of the sensor's capacitance.

Figure 20:
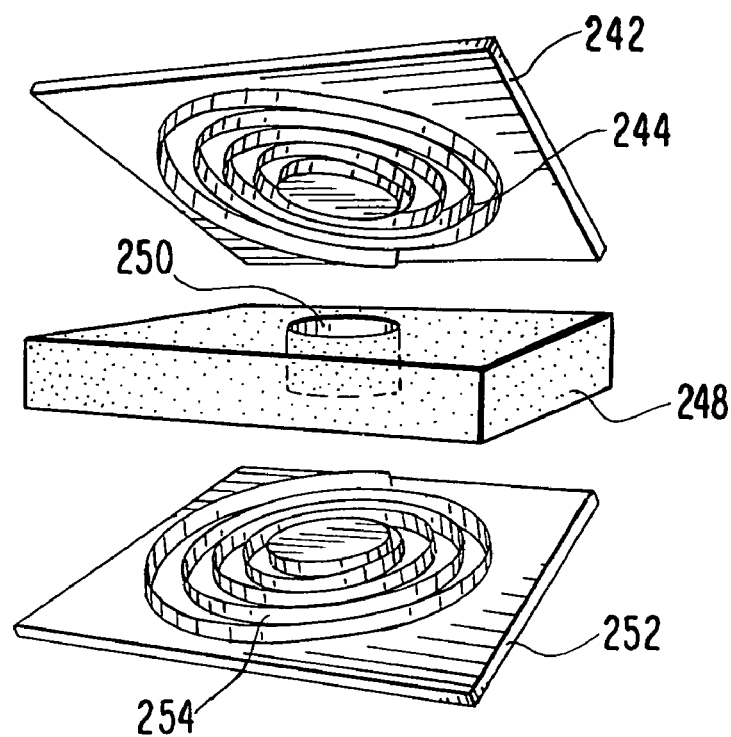
FIG. 20 is an exploded schematic representation of construction of one embodiment of a sensor.

In a preferred embodiment the sensor of the invention is constructed by laminating several layers of material together, as shown, for example, in FIG. 20. A first layer 242 is fabricated from a sheet of polyimide film (e.g. KAPTON, available from Du Pont) upon which a micro-machined copper pattern 244 is deposited. Pattern 244 preferably consists of a circular conductive segment in the center of the sheet surrounded by a spiral coil. A second layer 248 comprises a sheet of flexible adhesive through which hole 250 has been cut in the center. (Optionally there may be more than one such layer 248.) A final layer 252 is another sheet of polyimide film with a copper pattern 254 that is a mirror image of pattern 244. When assembled, the first, second, and third layers are aligned such that the holes in the middle adhesive layers are centered between the circular conductive segments in the middle of the two outer polyimide layers 242 and 252. In this way a capacitor (defined as an electric circuit element used to store charge temporarily, consisting in general of two metallic plates separated and insulated from each other by a dielectric) is formed. At the same time, the two metal spirals on the polyimide sheets 242 and 252 form an inductor component of a miniature electrical circuit.

The sensor exhibits the electrical characteristics associated with a standard LC circuit. An LC circuit is simply a closed loop with only two elements, a capacitor and an inductor. If a current is induced in the LC loop, the energy in the circuit is shared back and forth between the inductor and capacitor. The result is an energy oscillation that will vary at a specific frequency. This is termed the resonant frequency of the circuit and it can be easily calculated as its value is dependent on the circuit's inductance and capacitance. Therefore, a change in capacitance will cause the frequency to shift higher or lower in linear proportion to the change in the value of capacitance.

As noted above, the capacitor in the assembled pressure sensor consists of the two circular conductive segments separated by an air gap. If a pressure force is exerted on these segments it will act to deform the outer polyimide sheet and move the two conductive segments closer together. This will have the effect of reducing the air gap between them which will consequently change the capacitance of the circuit. The result will be a shift in the circuit's resonant frequency that will be in direct proportion to the force applied to the sensor's surface.

Because of the presence of the inductor, it is possible to electromagnetically couple to the sensor and induce a current in the circuit. This allows for wireless communication with the sensor and the ability to operate it without the need for an internal source of energy such as a battery. Thus, if the sensor is located within the sac of aortic aneurysm, it will be possible to determine the pressure within the sac in a simple, non-invasive procedure by remotely interrogating the sensor, recording the resonant frequency and converting this value to a pressure measurement. The readout device generates electromagnetic energy that penetrates through the body's tissues to the sensor's implanted location. The sensor's electrical components absorb a fraction of the electromagnetic energy that is generated by the readout device via inductive coupling. This coupling induces a current in the sensor's circuit oscillates at the same frequency as the applied electromagnetic energy. Due to the nature of the sensor's electro-mechanical system there exists a frequency of alternating current at which the absorption of energy from the readout device is at a minimum. This frequency is a function of the capacitance of the device. Therefore, if the sensor's capacitance changes, so will the frequency at which it minimally absorbs energy from the readout device. Since the sensor's capacitance is mechanically linked to the fluid pressure at the sensor's surface, a measurement of this frequency by the readout device gives a relative measurement of the fluid pressure. If calibration of the device is performed, then an absolute measurement of pressure can be made. See, for example, the extensive discussion in the Allen et al. patent, again incorporated herein by reference, as well as Gershenfeld et al., U.S. Pat. No. 6,025,725, incorporated herein by reference.

The pressure sensor is made of completely passive components having no active circuitry or power sources such as batteries. The pressure sensor is completely self-contained having no leads to connect to an external circuit or power source. Furthermore, these same manufacturing techniques can be used to add additional sensing capabilities, such as the ability to measure temperature by the addition of a resistor to the basic LC circuit.

Figure 21:
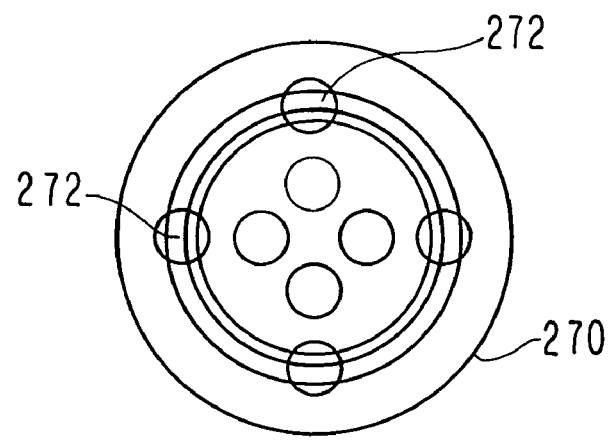
FIG. 21 is a schematic representation of an embodiment of the invention with distributed capacitance.

Several alternative configurations of the LC circuit design can be considered to address specific biological and manufacturing issues. For example, in one embodiment of the sensor the capacitor element consists of two plates that are separated by a suitable dielectric material, such as air, inert gas, fluid or a vacuum. To ensure the long term integrity of the sensor, various coatings could be applied to the surface or between the polymeric layers used to form the sensor. These coating can be used to provide a hermetic seal that will prevent leakage of body fluids into the cavity or permeation of the cavity material (gas, vacuum or fluid) out of the sensor. In an another embodiment of the invention, shown in FIG. 21, a sensor 270 has a multitude of capacitors 272 formed either as separate elements or as an array. In such a distributed capacitance configuration, there can be a more accurate and more sensitive measurement of pressure.

It is within the scope of the invention that the frequency response to the sensor will be in the range of from about 1 to about 200 $MH_z$, preferably from about 1 to about 100 $MH_z$, and more preferably from about 2 to about 90 $MH_z$, with a Q factor from about 5 to about 80, preferably from about 10 to about 70, more preferably from about 10 to 60.

In a further embodiment of the invention there is no direct electrical connection between the two sides of the LC circuit. Referring again to the sensor described in the Allen et al. patent, the device is constructed using multiple layers upon lie the necessary circuit elements. Disposed on the top and bottom layer are metal patterns constructed using micro-machining techniques which define a top and bottom conductor and a spiral inductor coil. To provide for an electrical contact between the top and bottom layers small vias or holes are cut through the middle layers. When the layers are assembled, a metal paste is forced into the small vias to create direct electrical connections or conduits. However, experimentation has shown that due to parasitic capacitance that is created between the top and bottom inductor coils, a vialess operational LC circuit can be created. This absence of via holes represents a significant improvement to the sensor in that it simplifies the manufacturing process and, more importantly, significantly increases the durability of the sensor making it more appropriate for use inside the human body.

Figure 22:
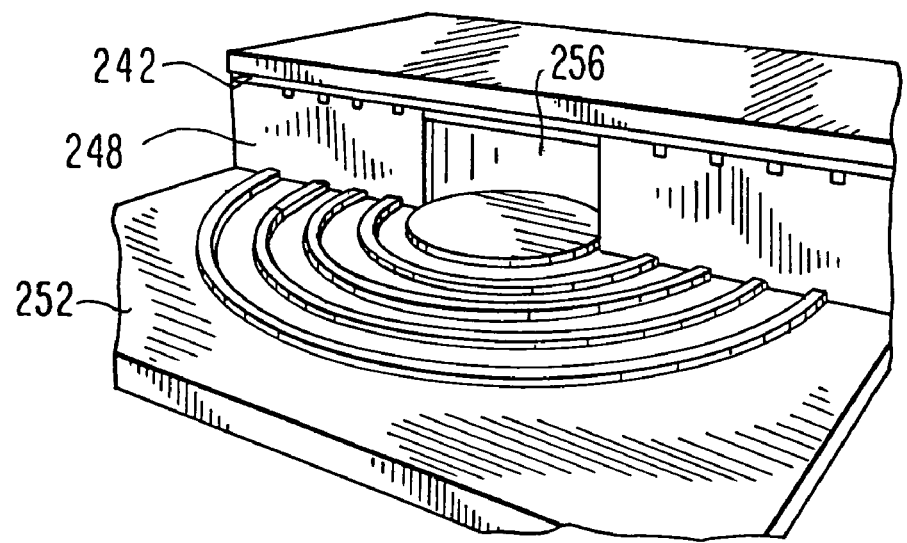
FIGS. 22 and 23 are each a schematic, partial cross-sectional view of an embodiment of a sensor according to the invention.
Figure 23:
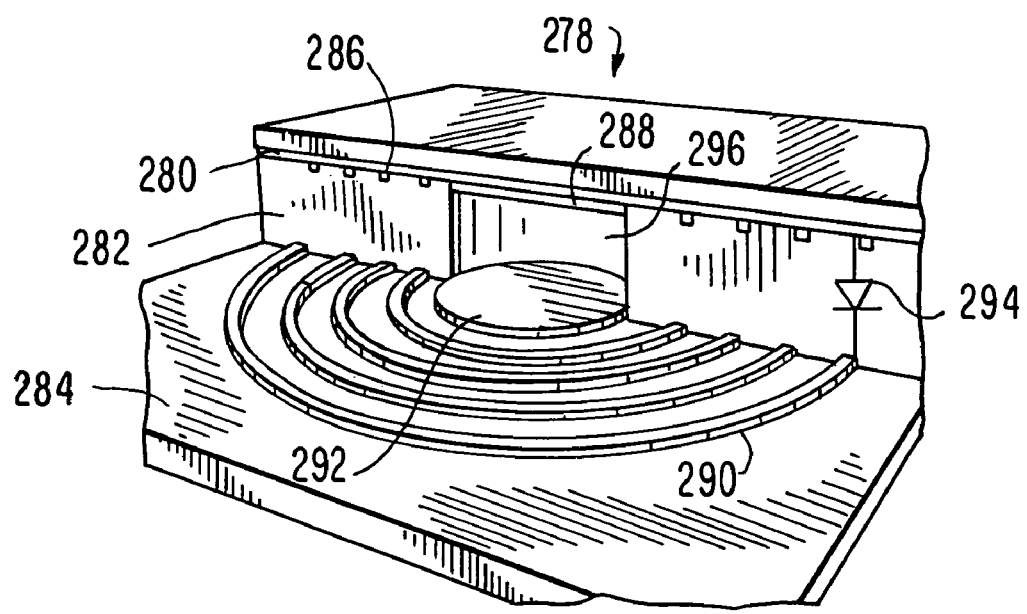

FIG. 22 is a partial cross-sectional review of the sensor shown in FIG. 20, where first layer 242, second layer 248, and third layer 252 are sandwiched together. A cylindrical space 256 comprises a pressure sensitive capacitor. No via holes are present. The sensor 278 shown in FIG. 23 comprises a first polyimide layer 280, a second, adhesive layer 282, and a third, polyimide layer 284. First layer 280 has a copper pattern comprising a coil 286 and a disk 288, and third layer 284 comprises a coil 290 and a disk 292. A cylindrical space 296 comprises a pressure sensitive capacitor. A diode 294 connected between coils 286 and 290 creates a non-linear sensor, i.e., a sensor where the frequency change is non-linear as compared to a change in pressure.

Figure 24:
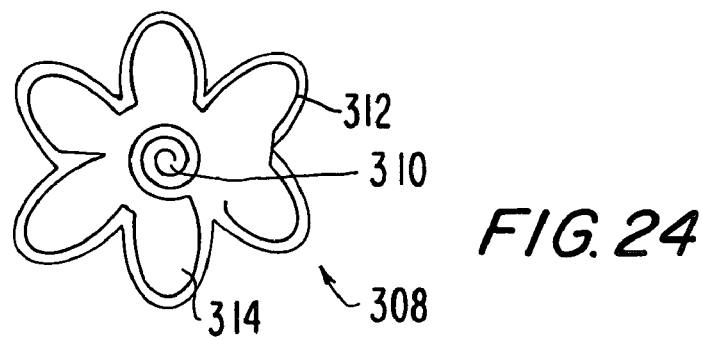
FIG. 24 is a schematic representation of an alternate shape for an embodiment of the invention.
Figure 25:
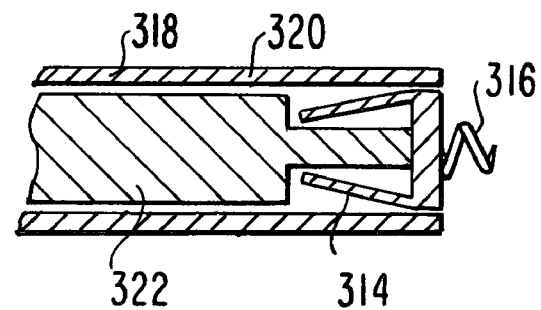
FIG. 25 is a cross-sectional view of the distal end of a delivery catheter with the embodiment shown in FIG. 24.

The design of the sensor is not limited to a specific geometric configuration. In the specific example noted above the inductor component is described as a spiral coil. Other embodiments of the sensor could utilize oval, rectangular or an amorphous shape. Specific electrical, mechanical and biologic advantages could be obtained by employing these various geometric designs. By way of example, a rectangular shaped sensor in which the ratio of length to width was greater than four would greater lend itself to catheter based delivery as is would minimize the radius of curvature required to position the folded device within a small diameter catheter. Alternatively, a more elaborate shape, such as one resembling the petals of a flower, would lend itself to more complex folding patterns that could facilitate delivery to specific areas of an aneurysm sac or an organ such as the heart. For example, in FIGS. 24 and 25, a flower-shaped sensor 308 has a capacitor surface 310 connected to a wire 312 that partly follows the outer configuration of sensor 308. Petals 314 fold so that sensor 308 with a distal anchor 316 can be "loaded" into a catheter 318. When the distal end 320 of catheter 318 is in position, a pushing rod member 322 is pushed distally to cause sensor 308 to be released from catheter 318 and attach to the inner surface of an organ such as the heart (not shown).

Figure 26:
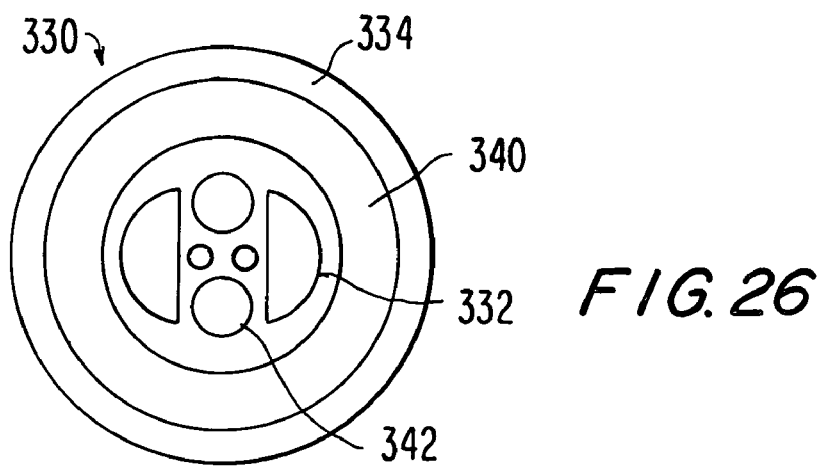
FIG. 26 is a schematic of another sensor according to the invention.

Another, preferred embodiment of a sensor is shown in FIG. 26, where circular sensor 330 comprises flexible cut-outs 332. The first outer layer 334 comprises a polymide substrate with a copper pattern comprising a coil 340 and several, from 2 to 6, disks 342 to form pressure sensitive capacitors. Sensor 330 also comprises at least one adhesive layer (not shown) and a third outer layer corresponding to the first outer layer (not shown). Preferably sensor 330 has at least one diode connecting the copper coils of the first and third layers.

The flexible cut-outs 352 facilitate, among other things, folding of sections of sensor 370 for placement in, or arrangement upon, a delivery catheter. The sections can be folded to create either a "Z" shape or, for example, a "U" shape. It is within the scope of the invention that variously numbered and shaped cut-outs could be used for particular applications.

Sensor 330 could be employed in the delivery catheters shown in FIGS. 12, 13, and 17, with a tether wire affixed by adhesive, as shown for sensor 52, for example. Sensor 330 could be used in either a Z- or U-configuration.

Figure 27:
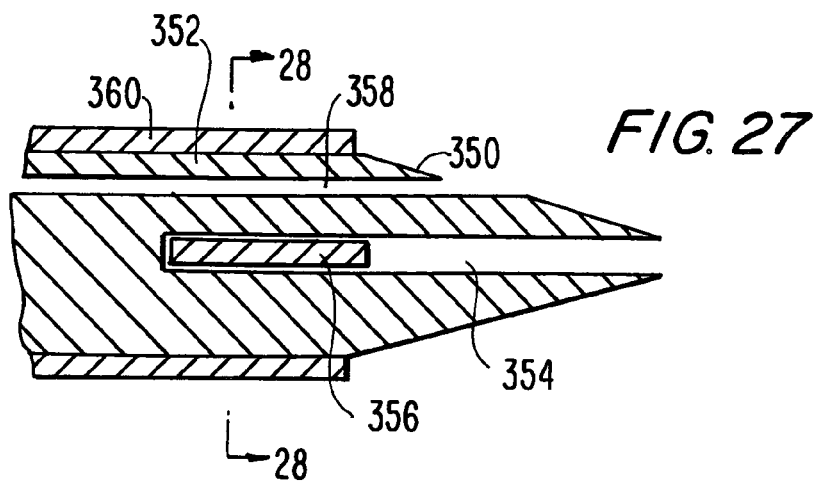
FIG. 27 is a cross-sectional schematic of the distal end of a delivery catheter.
Figure 28:
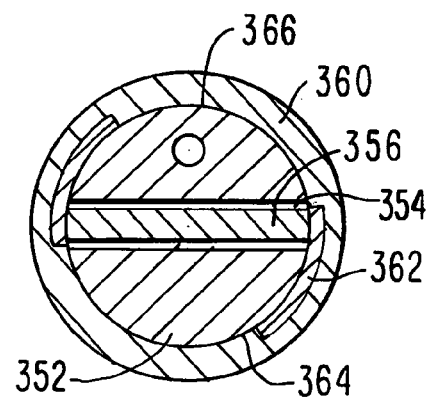
FIG. 28 is a longitudinal cross-sectional view across line 28-28 in FIG. 27.
Figure 29:
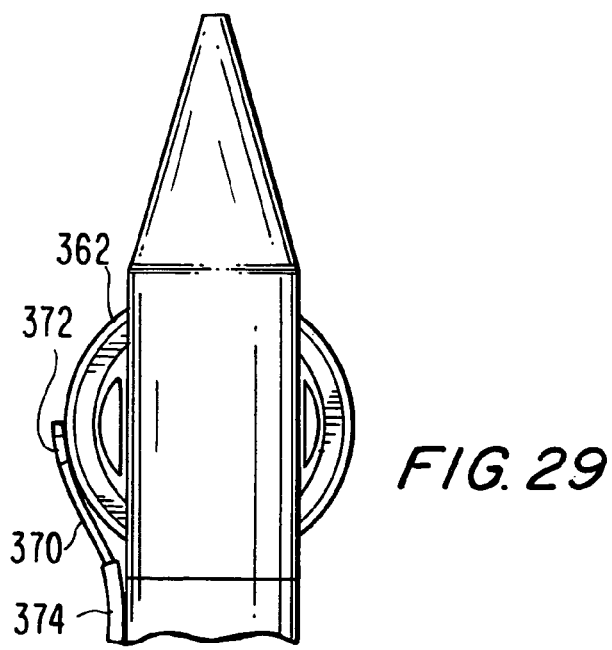
FIG. 29 is a top view of an embodiment of the delivery system shown in FIGS. 27 and 28.

In a delivery system shown in FIGS. 27 to 29, the distal portion 350 of the inner catheter 352 of a delivery catheter system comprises a slot 354 to receive sensor 356. Inner catheter 352 has a longitudinally extending lumen 358 to receive a guidewire (not shown).

During delivery to a desired location, such as an abdominal aortic aneurysm, an outer catheter sheath 360 encompasses distal portion 350 to hold sensor 356 in position. As shown in FIG. 28, sections 362 of sensor 356 extending outside slot 354 are held between the outer surface 364 of inner catheter 352 and the inner surface 366 of catheter sheath 360.

When the distal end of the delivery catheter is properly positioned, outer catheter sheath 360 is moved proximally to release folded sections 362. Then, outer catheter sheath 360 is moved distally to engage sections 362 and cause sensor 356 to disengage from slot 354.

At least one of sections 362 has a tether wire 370 attached at an adhesive point 372, as can be seen in FIG. 29. Tether wire 370 is slidably contained within tether sheath 374, which can be moved distally to disengage sensor 356 from tether wire 370. Tether wire 370 and tether sheath 374 preferably extend proximally to the proximal end of the delivery system. Tether wire 370 and tether wire 374 are positioned between outer catheter sheath 360 and inner catheter 352, preferably in a groove (not shown).

Further, the invention is not limited to the implantation of a single sensor. Since the biological environment within an aortic aneurysm is not necessarily homogeneous, multiple pressure sensors may be introduced into the aneurysm space, each being positioned at different locations. In this situation, each sensor may be designed with a unique signature (obtained by changing the resonant frequency of the sensor), so that the pressure measurement derived from one sensor can be localized to its specific position within the aneurysm.

Figure 32:
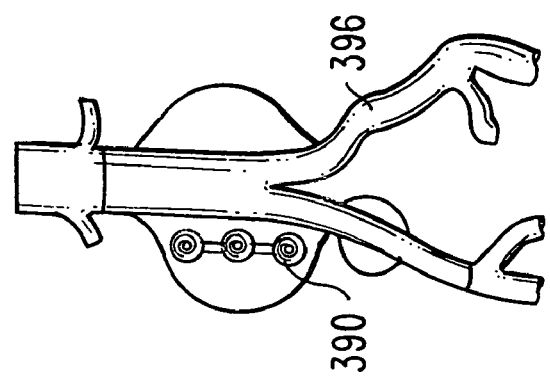
FIG. 32 is a partly cross-sectional schematic of the embodiment of FIG. 27 as placed in an aneurysm.
Figure 31:
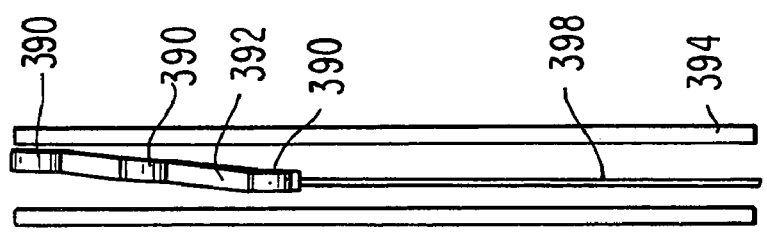
FIG. 31 is a cross-sectional lateral view of the embodiment of FIG. 30 in a catheter.
Figure 30:
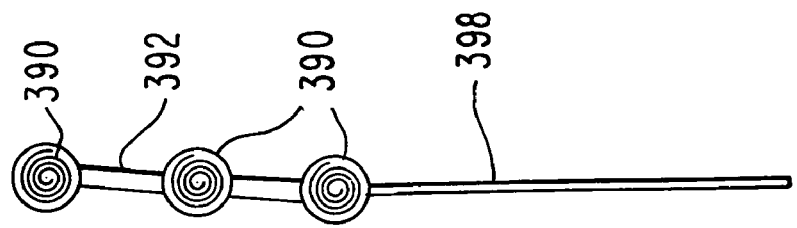
FIG. 30 is a perspective view of an embodiment of the invention having three sensors.
Figure 33:
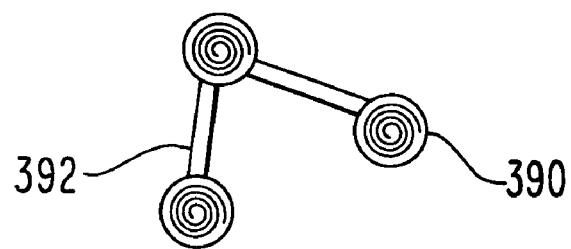
FIG. 33 is a variation of the embodiment of the invention shown in FIG. 30.

Clearly, if multiple sensors are used the same type of wire delivery system described above can also be employed to position the sensors within the aneurysm sac. For example, as shown in FIGS. 30 to 32, three sensors 390 can be linearly disposed along the length of a wire 392. All three sensors 390 would be deployed from a coaxial delivery catheter 394 as previously described, an endo-graft 396 would be introduced, and then the non-implantable segment 398 of the wire would be detached from the sensor array and removed from the body. The sensors 390 would remain secured to wire 392. This configuration would be advantageous for several reasons: pressure could be sensed from multiple areas of the aneurysm, the spacing between the sensors would remain constant and the sensors could not be displaced from the aneurysm sac during and after endo-graft implantation. In another embodiment of the same concept, wire 392 could be manufactured using a shape-memory or super-elastic alloy such as Nitinol. The wire could then be formed into a predetermined shape so that upon removing the sensors from the constraint of the coaxial catheter delivery system, the array of three (or more) sensors could take one of several preferred shapes within the aneurysm, as shown in FIG. 33.

Figure 34:
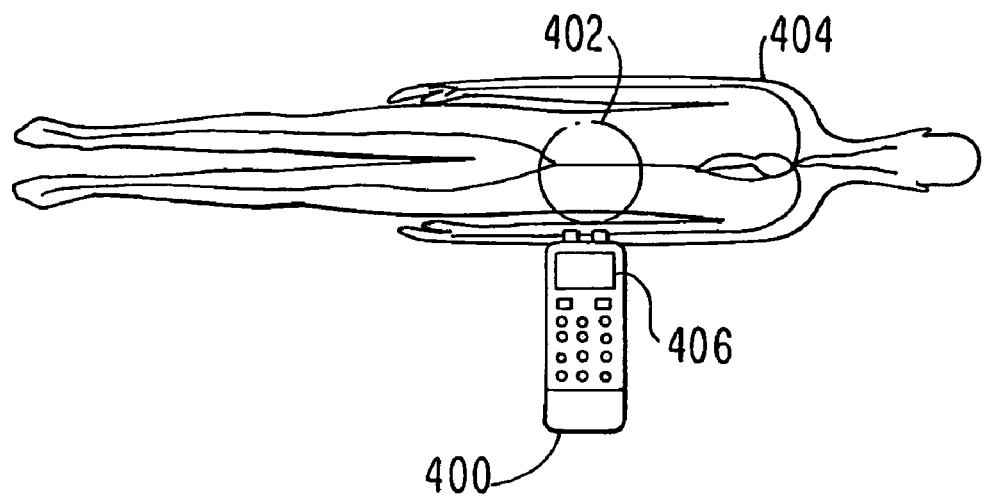
FIG. 34 is a drawing of a read-out device employed according to the invention.

When introduced into the sac of an abdominal aorta, the pressure sensor can provide pressure related data by use of an external measuring device. As disclosed in the Allen et al. patent, several different excitation systems can be used. The readout device generates electromagnetic energy that can penetrate through the body's tissues to the sensor's implanted location. The sensor's electrical components can absorb a fraction of the electromagnetic energy that is generated by the readout device via inductive coupling. This coupling will induce a current in the sensor's circuit that will oscillate at the same frequency as the applied electromagnetic energy. Due to the nature of the sensor's electro-mechanical system there will exist a frequency of alternating current at which the absorption of energy from the readout device is at a minimum. This frequency is a function of the capacitance of the device. Therefore, if the sensor's capacitance changes so will the frequency at which it minimally absorbs energy from the readout device. Since the sensor's capacitance is mechanically linked to the fluid pressure at the sensor's surface, a measurement of this frequency by the readout device can give a relative measurement of the fluid pressure. If calibration of the device is performed then an absolute measurement of pressure can be made The circuitry used to measure and display pressure is contained within a simple to operate, battery powered, hand-held electronic unit 400, as shown in FIG. 34. This unit 400 also contains the antenna 402 needed to perform the electromagnetic coupling to the sensor. The antenna may be integrated into the housing for the electronics or it may be detachable from the unit so that it can be positioned on the surface of the body 404 in proximity to the implanted sensor and easily moved to optimize the coupling between antenna and sensor. The antenna itself may consist of a simple standard coil configuration or my incorporate ferrous elements to maximize the coupling efficiency. The electronic device would feature an LCD or LED display 406 designed to clearly display the recorded pressure in physiologically relevant units such as mm HG. In an alternative embodiment, the display may be created by integrating a commercially available hand-held computing device such as a Palm® or micro-PC into the electronic circuitry and using this device's display unit as the visual interface between the equipment and its operator. A further advantage of this approach is that the hand-held computer could be detached from the read-out unit and linked to a standard desktop computer. The information from the device could thus be downloaded into any of several commercially available data acquisition software programs for more detailed analysis or for electronic transfer via hard media or the internet to a remote location.

Accordingly, the present invention provides for an impedance system and method of determining the resonant frequency and bandwidth of a resonant circuit within a particular sensor. The system includes a transmitting antenna, which is coupled to an impedance analyzer. The impedance analyzer applies a constant voltage signal to the transmitting antenna scanning the frequency across a predetermined spectrum. The current passing through the transmitting antenna experiences a peak at the resonant frequency of the sensor. The resonant frequency and bandwidth are thus determined from this peak in the current.

The method of determining the resonant frequency and bandwidth using an impedance approach may include the steps of transmitting an excitation signal using a transmitting antenna and electromagnetically coupling a sensor having a resonant circuit to the transmitting antenna thereby modifying the impedance of the transmitting antenna. Next, the step of measuring the change in impedance of the transmitting antenna is performed, and finally, the resonant frequency and bandwidth of the sensor circuit are determined.

In addition, the present invention provides for a transmit and receive system and method for determining the resonant frequency and bandwidth of a resonant circuit within a particular sensor. According to this method, an excitation signal of white noise or predetermined multiple frequencies is transmitted from a transmitting antenna, the sensor being electromagnetically coupled to the transmitting antenna. A current is induced in the resonant circuit of the sensor as it absorbs energy from the transmitted excitation signal, the current oscillating at the resonant frequency of the resonant circuit. A receiving antenna, also electromagnetically coupled to the transmitting antenna, receives the excitation signal minus the energy which was absorbed by the sensor. Thus, the power of the received signal experiences a dip or notch at the resonant frequency of the sensor. The resonant frequency and bandwidth are determined from this notch in the power.

The transmit and receive method of determining the resonant frequency and bandwidth of a sensor circuit includes the steps of transmitting a multiple frequency signal from transmitting antenna, and, electromagnetically coupling a resonant circuit on a sensor to the transmitting antenna thereby inducing a current in the sensor circuit. Next, the step of receiving a modified transmitted signal due to the induction of current in the sensor circuit is performed. Finally, the step of determining the resonant frequency and bandwidth from the received signal is executed.

Yet another system and method for determining the resonant frequency and bandwidth of a resonant circuit within a particular sensor includes a chirp interrogation system. This system provides for a transmitting antenna which is electromagnetically coupled to the resonant circuit of the sensor. An excitation signal of white noise or predetermined multiple frequencies is applied to the transmitting antenna for a predetermined period of time, thereby inducing a current in the resonant circuit of the sensor at the resonant frequency. The system then listens for a return signal which radiates from the sensor. The resonant frequency and bandwidth of the resonant circuit are determined from the return signal.

The chirp interrogation method for determining the resonant frequency and bandwidth of a resonant circuit within a particular sensor includes the steps of transmitting a multi-frequency signal pulse from a transmitting antenna, electromagnetically coupling a resonant circuit on a sensor to the transmitting antenna thereby inducing a current in the sensor circuit, listening for and receiving a return signal radiated from the sensor circuit, and determining the resonant frequency and bandwidth from the return signal.

Figure 35:
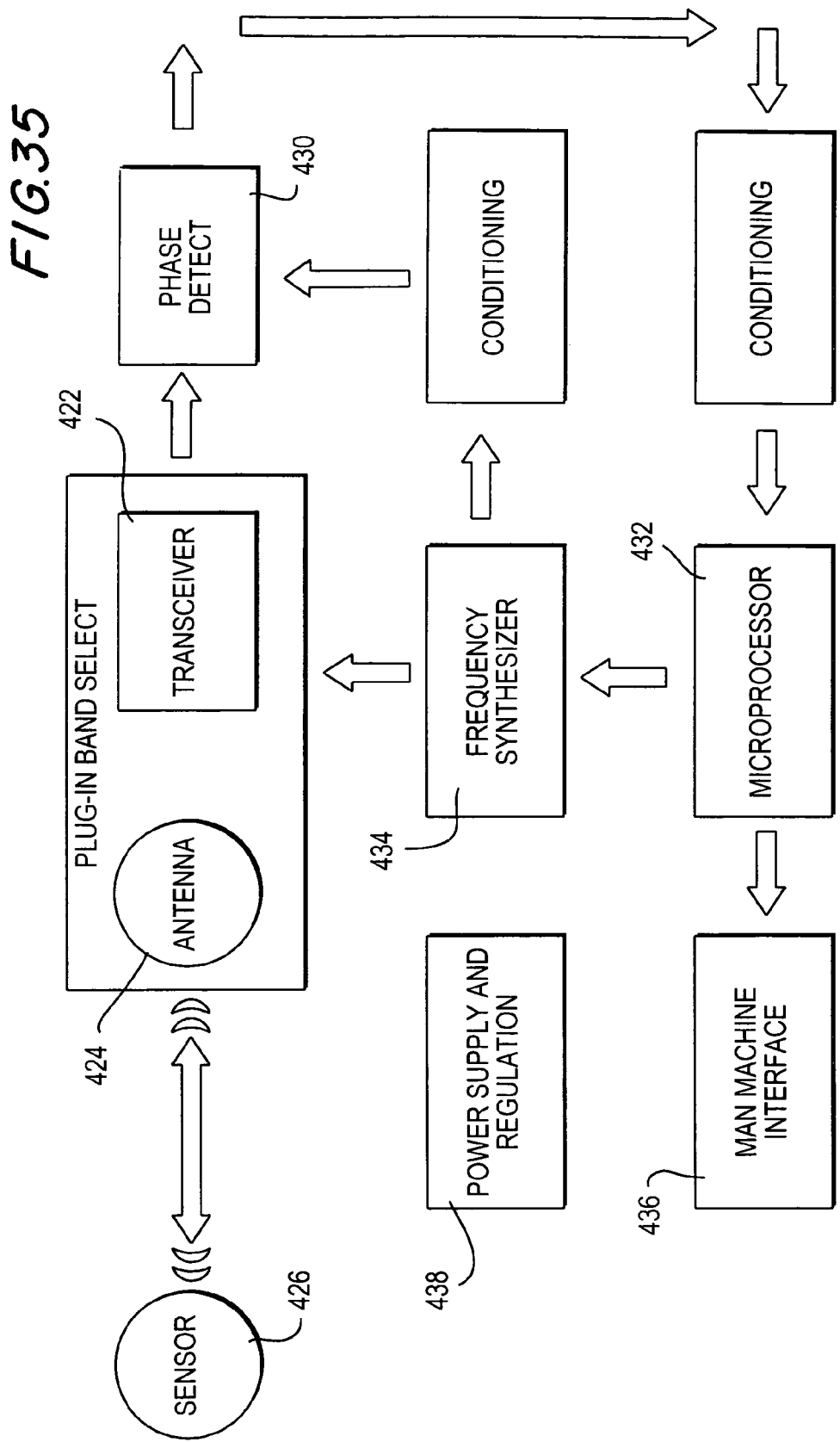
FIG. 35 is a block diagram of an electrical circuit useful according to the invention.

A representative block diagram of an electrical circuit that can be used to interrogate the sensor and determine the resonant frequency is shown in FIG. 35. A transmitter and receiver, i.e., a transceiver 422, has an antenna 424 for generating and receiving signals from a sensor 426. Transceiver 422 is an electronic or digital connection with a phase detector 430, a microprocessor 432, and a frequency synthesizer 434. Microprocessor 432 is in turn connected to an interface 436 such as a terminal. Power supply 438 regulates and provides electrical power to the system.

The present invention also provides an analog system and method for determining the resonant frequency of a resonant circuit within a particular sensor. The analog system comprises a transmitting antenna coupled as part of a tank circuit which in turn is coupled to an oscillator. A signal is generated which oscillates at a frequency determined by the electrical characteristics of the tank circuit. The frequency of this signal is further modified by the electromagnetic coupling of the resonant circuit of a sensor. This signal is applied to a frequency discriminator which in turn provides a signal from which the resonant frequency of the sensor circuit is determined.

The analog method for determining the resonant frequency and bandwidth of a resonant circuit within a particular sensor includes the steps of generating a transmission signal using a tank circuit which includes a transmitting antenna, modifying the frequency of the transmission signal by electromagnetically coupling the resonant circuit of a sensor to the transmitting antenna, and converting the modified transmission signal into a standard signal for further application.

The invention further includes an alternative method of measuring pressure in which a non-linear element such as a diode or polyvinylidenedifloride piezo-electric polymer is added to the LC circuit. A diode with a low turn-on voltage such as a Schottky diode can be fabricated using micromachining techniques. The presence of this non-linear element in various configurations within the LC circuit can be used to modulate the incoming signal from the receiving device and produce different harmonics of the original signal. The read-out circuitry can be tuned to receive the particular harmonic frequency that is produced and use this signal to reconstruct the fundamental frequency of the sensor. The advantage of this approach is two-fold; the incoming signal can be transmitted continuously and since the return signal will be at different signals, the return signal can also be received continuously.

The above methods lend themselves to the creation of small and simple to manufacture hand-held electronic devices that can be used without complication.

One additional concern regarding devices designated for long term implantation in the human body is maintenance of electrical stability over time as the environment the sensor has been placed in changes. Under this scenario the sensor's accuracy may drift from its original baseline. It would thus be desirable to have available to the user of the device, a method for determining if the sensor is functioning properly and also to be able to recalibrate the device anytime after it has been implanted. This invention therefore also includes a method of using acoustic energy to challenge the sensor and determining to what degree (if any) sensor performance has been degraded. In this method, energy in the ultrasound range is directed towards the sensor and a measurement is made of the mechanical resonance of the sensor membrane. This same measurement can be made at point after the sensor has been implanted. By comparing the values of these two measurements a determination of the degree of change in mechanical resonance frequency can be established. This value can then be used to create a calibration factor that can be applied to the pressure reading taken post-implantation in order to adjust the measured value to reflect the actual pressure within the aneurysm.

The preceding specific embodiments are illustrative of the practice of the invention. It is to be understood, however, that other expedients known to those skilled in the art or disclosed herein, may be employed without departing from the spirit of the invention of the scope of the appended claims.

We claim:

1. A flexible sensor for wirelessly determining a physical property of a patient, which sensor comprises a self-contained resonant circuit comprising a capacitor and an inductor, and
   wherein the circuit is variable in response to the physical property of the patient,
   wherein the sensor is comprised of biocompatible materials,
   wherein the sensor is sufficiently flexible to be folded for delivery percutaneously,
   wherein the sensor is disk-shaped, and
   wherein the sensor has an anchoring system attached to a flat surface of the sensor.

2. The sensor of claim 1, wherein the capacitor is variable in response to the physical property of the patient.

3. The sensor of claim 1, wherein the inductor is adapted to allow inductance of a current in the resonant circuit when the sensor is subjected to a time-varying electromagnetic field.

4. The sensor of claim 1, wherein the physical property is pressure or temperature.

5. The sensor of claim 4, wherein the physical property is pressure.

6. The sensor of claim 5, wherein sensor is designed to respond to a range of pressure corresponding to a range of pressure normally found within a vascular aneurysm.

7. The sensor of claim 5, wherein the sensor is designed to respond to a range of pressure corresponding to a range of pressure normally found in a chamber of the patient's heart.

8. The sensor of claim 1, wherein the sensor has one or more metallic members attached to a flat surface of the sensor.

9. The sensor of claim 1, wherein the sensor has one or more metallic members layered within the sensor.

10. The sensor of claim 1, wherein the sensor has a metallic ring surrounding a portion of the edge of the sensor.

11. The sensor of claim 1, wherein the anchoring system is a coil.

12. The sensor of claim 1, wherein the anchoring system has radial projections in an umbrella shape.

13. The sensor of claim 1, wherein the sensor has at least one cutout to facilitate folding.

14. The sensor of claim 1, wherein the sensor is capable of being folded into a Z-shape.

15. The sensor of claim 1, wherein the sensor is capable of being folded into a U-shape.

16. The sensor of claim 1, wherein a safety wire is attached to one surface of the sensor.

17. The sensor of claim 16, wherein the safety wire has a sheath.

18. The sensor of claim 17, wherein the sheath is capable of being slid distally to free the safety wire from the sensor.

19. The sensor of claim 16, wherein the safety wire is attached to the sensor at an adhesive point.

20. The sensor of claim 19, wherein the adhesive point comprises an epoxy or a cyanoacrylate material.

21. The sensor of claim 1, wherein the primary material of construction is flexible, biocompatible polymer or co-polymer.

22. The sensor of claim 21, wherein the polymer or co-polymer is selected from the group consisting of polyamide, polyethylene teraphthalate, polytetrafluoroethlyene, and co-polymers thereof.

23. The sensor of claim 1, wherein there are no conductive connections or via holes to provide a direct electrical conduit between an upper inductor coil and a lower inductor coil.

24. The sensor of claim 1, further comprising a non-linear element that responds in a non-linear manner to an excitation signal.

25. The sensor of claim 1, wherein the capacitor comprises an array of smaller capacitors.

26. The sensor of claim 1, wherein the sensor has a loading tab member.

27. The sensor of claim 1, wherein the sensor is capable of being folded so that a middle section remains substantially flat and the outer edges or surfaces are at substantially a 90° angle to said middle section.

28. The sensor of claim 27, wherein the sensor is substantially daisy-shaped.

29. A sensor delivery system comprising:
   a sensor comprising a self contained resonant circuit comprising a capacitor and an inductor, wherein the circuit is variable in response to the physical property of the patient, and wherein the sensor is sufficiently flexible to be folded for delivery percutaneously, and
   a delivery catheter comprising an inner tubular member having an outer surface and an outer tubular member having an inner surface, the outer surface of the inner tubular member and the inner surface of the outer tubular member defining an annular space therebetween;
   wherein the sensor is contained within said annular space.

30. The delivery system of claim 29, wherein the outer tubular member is slidable in the proximal direction to release the sensor.

31. The delivery system of claim 29, wherein the delivery catheter has an atraumatic tip.

32. The delivery system of claim 31, wherein the atraumatic tip is attached to the distal end of the inner tubular member.

33. The delivery system of claim 29, comprising an annular stop proximal to the sensor in the annular space.

34. The delivery system of claim 29, wherein the annular space in the delivery catheter is configured such that several sensors can be contained within the catheter.

35. The delivery system of claim 29, wherein the sensor has a safety wire attached thereto and said safety wire extends proximally in a longitudinally extending groove in the inner surface of the outer catheter, the outer surface of the inner catheter, or both.

36. The delivery system of claim 29, wherein the sensor is one of a plurality of sensors, and wherein each of said plurality of sensors is tuned to operate at a different resonant frequency.

37. The delivery system of claim 36, wherein said plurality of sensors comprises two sensors.

38. The delivery system of claim 36, wherein said plurality of sensors comprises three sensors.

39. The delivery system of claim 29, wherein the sensor is in a curved configuration within the delivery catheter.

40. The delivery system of claim 29, wherein the sensor is in a Z-shaped configuration within the delivery catheter.

41. The delivery system of claim 29, wherein the sensor is in a U-shaped configuration within the delivery catheter.

42. The delivery system of claim 29, wherein the inner catheter has a longitudinally extending lumen so that the delivery system is capable of being slidably positioned over a guidewire.

43. A sensor delivery system comprising:

a sensor comprising a self-contained resonant circuit comprising a capacitor and an inductor, wherein the circuit is variable in response to the physical property of the patient, and wherein the sensor is sufficiently flexible to be folded for delivery percutaneously; and a delivery catheter comprising an inner tubular member having an outer surface and an outer tubular member having an inner surface, the outer surface of the inner tubular member and the inner surface of the outer tubular member defining an annular space therebetween;

wherein the sensor is contained within the annular space, wherein the sensor has a tab member that engages a reciprocal slot in the inner tubular member, wherein the outer tubular member has a slit, and wherein rotation of the inner tubular member causes the sensor to advance through the slit.

44. The delivery system of claim 43, wherein the inner catheter has a longitudinally extending lumen so that the delivery system is capable of being slidably positioned over a guidewire.

* * * * *